United States Patent
Koch et al.

[11] Patent Number: 5,183,667
[45] Date of Patent: Feb. 2, 1993

[54] THERAPEUTIC IMMUNOSTIMULATION BY GLOMBRELLA CINGULATA

[75] Inventors: Helmut Koch, Tervuren; Harald W. W. Röper, Brussel, both of Belgium

[73] Assignee: Cerestar Holding B.V., Sas van Gent, Netherlands

[21] Appl. No.: 677,485

[22] Filed: Mar. 29, 1991

[30] Foreign Application Priority Data

Apr. 5, 1990 [GB] United Kingdom ................ 9007730

[51] Int. Cl.$^5$ ........................ A61K 9/28; A61K 31/70; A61K 9/48; A01N 25/34
[52] U.S. Cl. .................................. 424/474; 424/400; 424/408; 424/422; 424/451; 424/464; 435/254; 514/23; 514/885
[58] Field of Search ................ 424/400, 408, 422, 451, 424/464, 474; 435/254; 514/23, 885; 536/1.1, 114

[56] References Cited

PUBLICATIONS

"Optimization & Characterization of an Extracellular Polysaccharide Produced by Glomerella-Cingulata"; Sarkar et al.; Biotechnol, Letter 7(9), 1985 631–636 (Full citation).

"Use of Modified Beta-Glucanderius for Immune System Activation for Treating Immune Compromised Patients in Surgery, Chemotherapy Infectious Disease Treatment etc.", Jamas et al., WO 9103248 (Abstract).

Primary Examiner—Thurman K. Page
Assistant Examiner—Carlos Azpuru
Attorney, Agent, or Firm—Cushman, Darby & Cushman

[57] ABSTRACT

An immune-stimulatory or tumor treatment agent, optionally in a pharmaceutically acceptable carrier or diluent, comprises extracellular $\beta$-glucan produced by Glomerella cingulata CMI CC 330957 or by mutants or variants thereof.

1 Claim, 2 Drawing Sheets

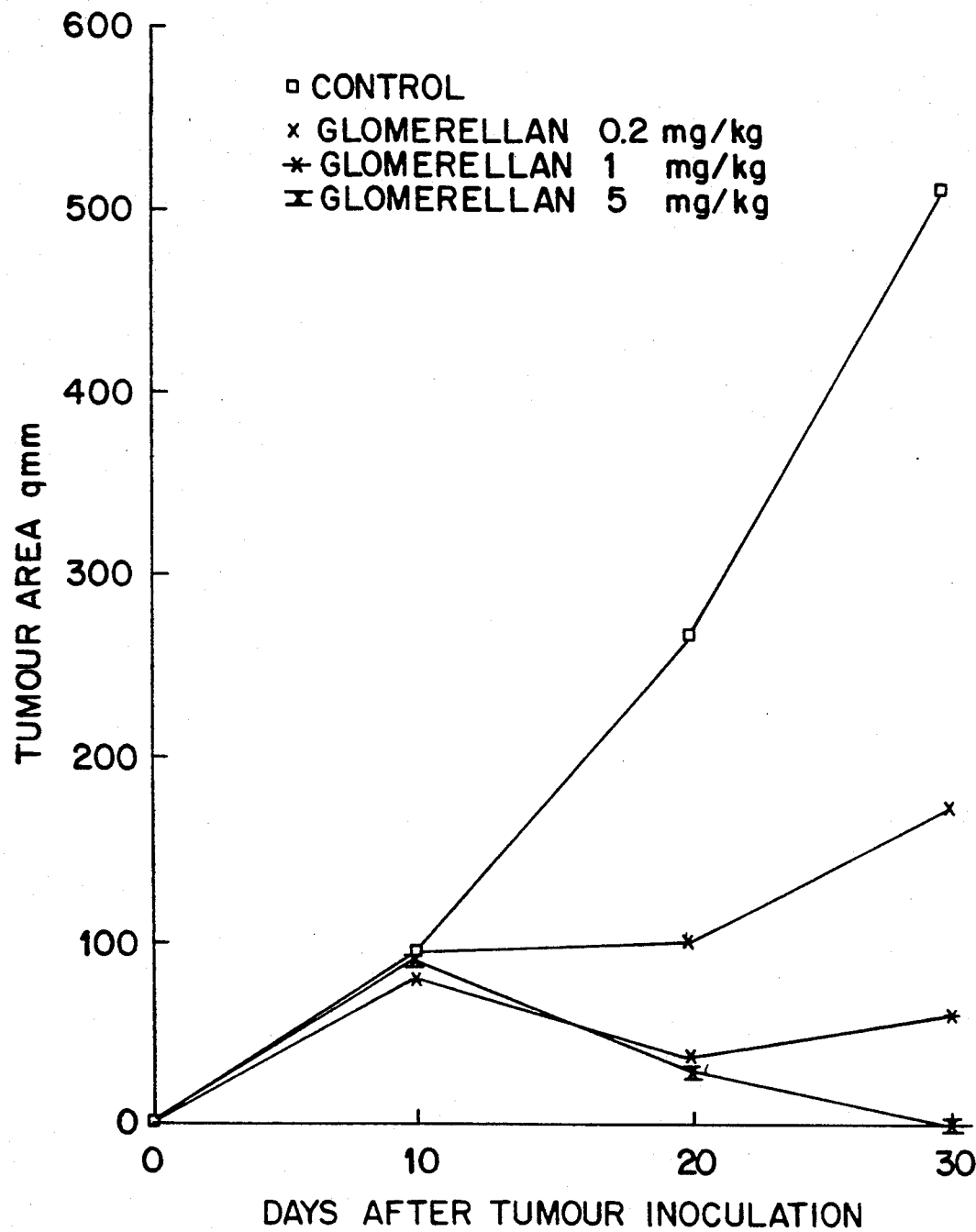

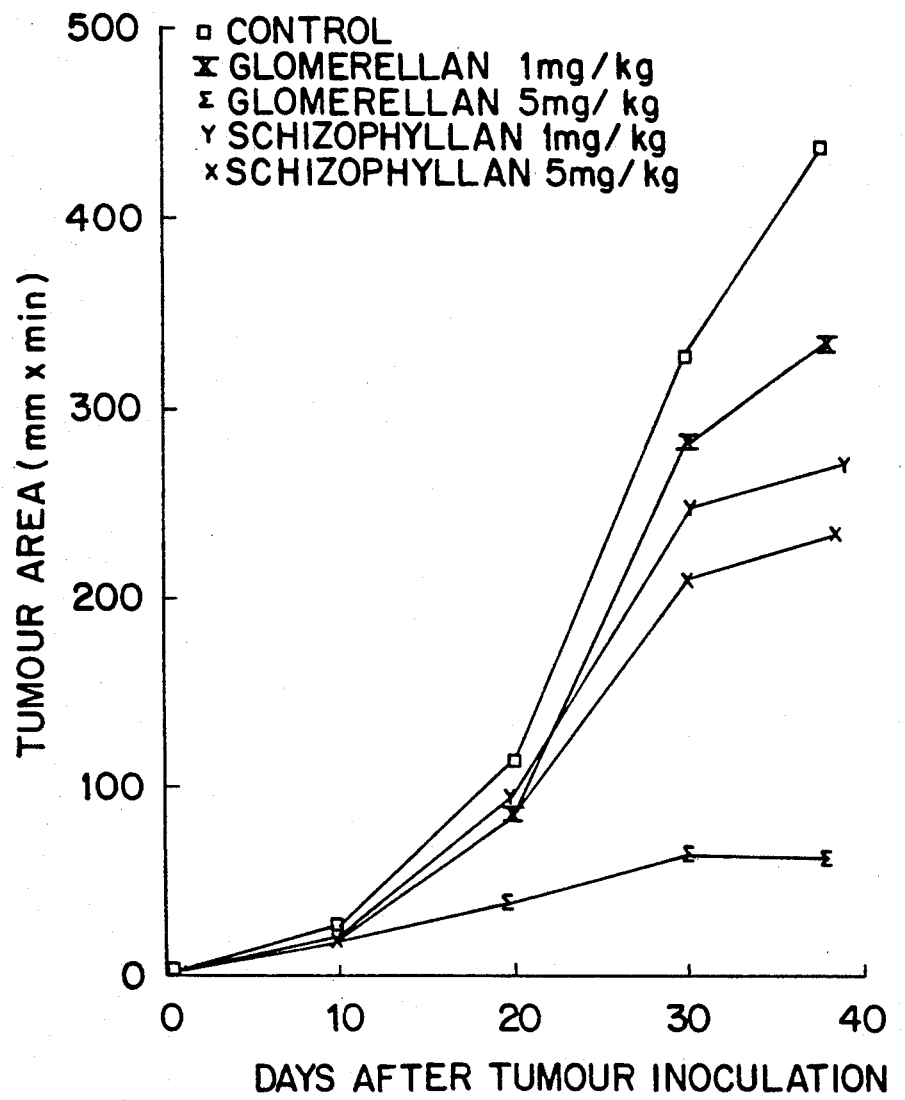

THERAPEUTIC IMMUNOSTIMULATION BY GLOMBRELLA CINGULATA

The present invention relates to an immune-stimulatory and anti-tumor composition comprising a beta-glucan produced by a strain of *Glomerella cingulata*.

An article by G. Franz in Farmaceutische Tijdschrift voor België 64c 74 g N°4, July-August 1987 describes the anti-tumour activity of certain polysaccharides the activity being explained by postulating that the polysaccharides stimulate the immune system. These anti-tumour polysaccharides include glucans with different types of glycosidic linkage but certain structural features are said to be common to the more active compounds. Thus, beta-1,3-linkages are present in the main chains of the active glucans while beta-1,6-branch points seem to be another structural requirement for anti-tumour activity. In addition polysaccharides which are completely insoluble in water are said to be inactive. The article reports that three polysaccharides are in clinical use in Japan namely two beta-1,3-glucans with beta-1,6-glucopyranosidic branches for every third glucose unit from Schizophyllum commune and Lentinus edodes respectively and a beta-1,4-glucan with beta-1,6-glucopyranosidic branches for every fourth glucose unit from Coriolus versicolor.

G. Franz reports in the article referred to in the preceding paragraph that experiments with a beta-1,3-beta-1,6-branched glucan from the cell walls of Phytophtora parasitica also showed promising results. In this case the glucan structure is similar to the Schizophyllan glucan in having a beta-1,3-backbone and regular 1,6-branch points but, in addition, it has beta-1,3-linkages in the side chain.

An article by J. M. Sarkar, G. L. Hennebert and J. Mayaudon in Biotechnology Letters Vol. 7, No. 9, 631–636 (1985) reports the isolation of a new strain of *Glomerella cingulata* which produces an extracellular highly viscous polysaccharide in a simple mineral medium. The article describes the optimum conditions for the production and characterisation of the extracellular glucan (designated "Glomerellan") and suggests that the product could find use as a thickener, binder or suspension agent in foodstuffs, cosmetics, pharmaceuticals, drilling muds, sizes and coatings for paper and textiles etc.

Structural investigations have shown that soluble Glomerellan is composed exclusively of glucose units. The amounts of single linkage types, determined by methylation amount to 23% 1-glc., 47% 1,3-glc., 25% 1,3,6-glc. and smaller portions of 1,6-bound glucose. Every third glucose unit of the main chain of Glomerellan, which is beta-1,3-linked, has a side chain which is 1,6-linked. The side chains are composed perdominantly of single glucose units. From the $^{13}$C-NMR spectrum beta-binding can be established. The molecular weight of Glomerellan is about 850,000 d.

The experimental work reported in the Article by G. Franz used Sarcoma 180 tumour as the basic screening model for testing the anti-tumour effects of the polysaccharides. Sarcoma 180 is an allogeneic tumour but for comprehensive clinical application activity against syngeneic tumours should also be possessed by an anti-tumour agent. We have now found that while the Glomerellan described by Sarkar et al has comparable anti-tumour activity to the commercially available Schizophyllan when tested against the allogeneic tumour Sarcoma 180 it is, surprisingly, far more effective than Schizophyllan when tested against a synogeneic tumour, fibrosarcoma DBA/2-MC.SC-1.

Accordingly, the invention comprises extracellular beta-glucan produced by *Glomerella cingulata* CMI CC 330957 (Glomerellan) or by mutants or variants thereof for use as an immune-stimulatory or tumour treatment agent.

The invention also includes an immune stimulatory and/or anti-tumour composition comprising, in an amount showing immune stimulatory and/or anti-tumour action, an extracellular beta-glucan produced by *Glomerella cingulata* CMI CC 330957 (Glomerellan) or by mutants or variants thereof and a pharmaceutically acceptable carrier or diluent.

BRIEF DESCRIPTION OF THE DRAWINGS

FIG. 1 shows the rate of sarcoma development in Glomerellan-treated versus control groups.

FIG. 2 shows the rate of fibrosarcoma development in Glomerellan-treated versus control groups.

A description of Glomerella cingulata is as follows:

*Glomerella cingulata* (Stoneman) Spaulding & von Schrenck, in Bot. Gaz. 26 : 101, 1898 and U.S.D.A. Bur. Pl. Ind. Bull. 44: 29, 1903.

Anamorph (conidial):

*Collectotrichum gloeosporioides* (Penzig) Penzig, in Fungi Agrum 2 : 6, 1882.

syn. *Vermicularia gloeosporioides* Penzig, in Michelia 2: 450, 1880.

syn. *Colletotrichum piri* Noack, in Bol. Inst. agr. Est. Sao Paulo 9 : 7, 1854.

Class Asomycotina, Order Sphaeriales, Family Polystigmataceae. Description of the species on natural substrate:

Ascosporic state: Perithecia obsolete or gathered in a stromatic layer, 85–300 μm diam., globose or flask-shape, wall of few layers of brown, polygonal and flattened cells, apical ostiolum minute or papilliform, provided with internal hyaline, sometimes merging periphyses. Asci parallel, cylindrical, unitunicate, 35–80×8–14 μm, apically operculate, octosporic. Ascospores elliptical, to naviculiform, unicellular, hyaline, 9–30×3–8 μm, septate and producing a fuliginous 5–8 μm diam. appresorium when germinating. Paraphyses filiform, hyaline, mucilaginous.

Conidial state: Acervuli erumpent from the host tissues, on a stromatic layer, forming parallel conidiphores mixed with few straight, black, pointed, up to 120 μm long, septate setae. Conidiophores short, unbranched, apically hyaline, tapered, phialidic, without collarette. Conidia mucilaginous, hyaline, rose to orange in mass, cylindrical to reniform, 12–22×4–6 μm, developing a 5–8 μm diam. appresorium when germinating.

The strain of the fungus which produces the extracellular glucan Glomerellan was isolated from a black rot of a fruit of *Pyrus communis* var. Claps Favorit in Hacquegnies, Prov. Hainaut, Belgium, in 1966 by G. L. Hennebert, and has been deposited with the C.A.B. International Mycological Institute Culture Collection, Ferry Lane, Kew, Surrey TW9 3AF, United Kingdom, as accession No. CMI CC 330957. It is also deposited in the Mycotheque Université Catholique de Louvain as MUCL 1232.

A description of the strain is as follows (Abbreviations: MYA2:malt extract 2%, yeast extract 0.3% in gelose; PDA: potato extract, dextrose 2% in gelose;

DYAA:dextrose 1%; yeast extract 0.3%, asparagine 0.1%, and salts in gelose). Mycelium first white, rapidly becoming light mouse grey, then dark grey, reverse olive grey becoming dark greenish grey, on MYA2, PDA and DYAA. Growth rate of 9 cm diam./5 days on MYA2 and DYAA and 9 cm dia./4 days on PDA. Aerial hyphae fluffy and high, septate and branched, 2-7 μm diam. No conidiophores and non conidia produced any more. No perithecia observed.

The glucan can be prepared by aerobic fermentation of a culture medium standard for fungal fermentations, i.e. one containing sources of carbon, nitrogen, phosphate, magnesium potassium, sulphate and iron. As the preferred carbon source dextrose of sucrose may be used, while papetone, yeast extract, asparagine, corn steep liquor, or other conventional materials are suitable as a source of nitrogen. Dextrose and corn steep liquor are the preferred sources of carbon and nitrogen, respectively. The starting pH should be within the range of 4.5-8.0, preferably about 7.5, and the temperature should be within the range of 22° C.-38° C., preferably about 35° C. The cultivation should be conducted for at least 3 days, 4-5 days normally being sufficient for maximum production. At the end of the cultivation the culture medium is viscous and should be diluted with water prior to centrifugation to remove the mycelium. The Glomerellan may then be recovered by precipitation by adding the aqueous dispersion to a lower aliphatic alcohol. Suitable alcohols include ethanol and isopropanol.

glomerellan is truly soluble in both cold and hot water which is important for maximum therapeutic activity.

glomerellan may be used to stimulate the immune system of an animal e.g. in the treatment of immunosuppressive conditions such as AIDS and in the treatment of caner. In medical or veterinary use, Glomerellan may be administered with a pharmaceutically acceptable carrier or diluent and, depending upon the dosage required, the Glomerellan may form 1 to 90% by weight of the total weight of Glomerellan plus carrier. The carrier may be chosen so as to provide an orally administrable form e.g. as a powder, granule, capsule, tablet, coated table, syrup or aqueous preparation, or as a parenterally administrable form such as a preparation for injection. Suitable carriers, apart from water, include calcium phosphate, calcium carbonate, glucose, lactose, sucrose, dextrins, starch, sorbitol, mannitol, talc, kaolin, carboxymethylcellulose, methylcellulose, sodium alginate, gum arabic, tragacanth gum, gelatin, physiological saline, ethanol, propylene glycol, and glycerine.

The Glomerellan may be administered by procedures which are standard for the treatment of tumours and for stimulating the immune system e.g. by subcutaneous, intramuscular or intravenous injection or by oral administration etc. The dosage and mode of administration will depend upon a variety of factors such as the patient, nature of the complaint being treated etc. An example of a suitable dosage level is 1 to 5000 mg/kg body/day for oral administration and 0.5 to 5000 mg/kg body/day by injection.

Glomerellan may advantageously be used in combination with other forms of treatment of tumours. for example, Glomerellan may be used together with other drugs or with hormonal compositions or as a follow-up to surgical treatment.

The invention will now be further described with reference to the following Examples.

EXAMPLES 1 TO 3 PREPARATION OF GLOMERELLAN

EXAMPLE 1

250 ml shaken flasks each containing 100 ml of the following medium:dextrose 5%, peptone 0.2%, $K_2HPO_4$ 0.2%, $MgSO_4$ $7H_2O$ 1.04%, NaCl 0.2%, $(NH_4)Fe(SO_4)_2$ $12H_2O$ 0.001% at pH 7.5 were inoculated with a spore suspension and incubated at 27° C. for 4 days. This preculture was used as 5% inoculum for 1 liter Erlemeyer cultures (400 ml of the same medium) which were incubated under the same conditions. These cultures were used as seed cultures for a 100 liter fermentor.

80 liters of the above mentioned culture medium were inoculated with 3-4 liters inoculum. The temperature was 27° C.; the impeller speed 350 rpm and aeration 0.15 vvm. After 48 hours culture the impeller speed was increased up to 450 rpm and then up to 550 rpm at 0.25 vvm aeration after 72 h. On the fourth day the culture was stopped.

The medium was diluted twice (160 l) with water and centrifuged to remove the mycelium. The clear supernatant liquid was mixed into 66% isopropanol and the precipitated product dried at 50°-60° C. under vacuum. The product was then ground to a very light white powder. The yield was 290 g.

EXAMPLE 2

The seed cultures prepared following Example 1 were used to inoculate 2×2 L fermentors containing the same medium as in Example 1 except that dextrose was replaced by sucrose in one case. The cultures were stirred at 450 rpm at 27° C..and the aeration rate was 0.3 vvm. After 4 days, the culture was stopped and the product precipitated as described in Example 1.

Product yields were 1.6 g/l and 2 g/l in the case of sucrose and dextrose respectively, indicating that dextrose is a somewhat preferable carbon source as compared to sucrose.

EXAMPLE 3

The same assay as described in Example 2 was carried out with dextrose as the sugar but substituting peptone by yeast extract, corn steep liquor, asparagine or a casein hydrolysate.

The results shown in the following table indicate that corn steep liquor was the best nitrogen source giving the highest yields.

| NITROGEN SOURCE (2 g/l) | GLOMERELLAN (g/l) |
|---|---|
| Corn steep liquour | 2.25 |
| Yeast extract | 2.12 |
| Peptone | 2.00 |
| Asparagine | 1.57 |
| Casein hydrolysate | 1.54 |

Evaluation of Glomerellan as an Anti-Tumour Agent

1. Sarcoma 180

Female CD1-mice were used in the test and at day 0 $5 \times 10^6$ cells of Sarcoma 180 were subcutaneously injected. The test period was 30 days during which the increase in tumour size was measured and at the end of the period the individual tumours were excised and weighed.

The Glomerellan was dispersed in a saline carrier (the control animals being treated with the carrier alone) and the carrier injected interperitoneally at 0+24 hours and then at 24 hour intervals for 10 consecutive days. The rate of inhibition of the tumour growth was estimated by comparing the average tumour weight of the Glomerellan-treated animals with the average tumour weight of the control group. The development of tumour area with time is shown in FIG. 1 attached to this specification while the results of the tumour weight estimations were as follows

|  | Evaluations of Tumours at Day 30 | | | | |
|---|---|---|---|---|---|
|  | Dose (mg/kg) | Average Tumour weight (g) | Inhibition* % | Complete** Regression | Significance++ p < |
| control | — | 6.39 | — | 0/10 | — |
| Glomerellan | 0.2 | 2.46 | 62 | 5/10 | n.s.+ |
| Glomerellan | 1.0 | 0.72 | 89 | 8/10 | 0.01 |
| Glomerellan | 5.0 | 0 | 100 | 9/9 | 0.001 |

*Inhibition: [(C − T) ÷ C] where average tumour weight of control group = C average tumour weight of treated group = T
**Number of tumour-free mice/number of treated mice
+n.s. = not significant
++Evaluated according to Student's T-test.

2. Comparative evaluation of Glomerellan and commercial Schizophyllan with Sarcoma 180

The procedure of (1) was repeated using Glomerellan and a commercially available sample of Schizophyllan. The results were as follows:

|  | Evaluation of Tumours at Day 30 | | | | |
|---|---|---|---|---|---|
|  | Dose mg/kg | Average Tumour weight (g) | Inhibition % | Complete regression | Significance p < |
| Control | — | 8.6 | — | 0/9 | — |
| Glomerellan | 5 | 0.7 | 92 | 6/8 | 0.0001 |
| Schizophyllan | 5 | 0.3 | 97 | 7/10 | 0.0001 |

3. DBA/2-MC.SC-1 fibrosarcoma

The evaluation was the same as for Sarcoma 180 with the exception that pieces of tumour of about 1 square millimeter size were subcutaneously transplanted into female DBA/2-mice. Test solutions were injected interperitoneally three times a week and the test period was 38 instead of 30 days. The results of the tumour weight estimations compared with Schizophyllan are shown below. The rate of tumour development with time is given in FIG. 2 attached to this specification.

|  | Dose mg/kg | Average Tumour weight (g) | Inhibition % | Complete regression | Significance p < |
|---|---|---|---|---|---|
| Control | — | 4.28 | — | 0/13 |  |
| Glomerellan | 1 | 4.32 | −0.1 | 0/10 | n.s. |
|  | 5 | 0.66 | 85 | 6/10 | 0.0001 |
| Schizophyllan | 1 | 3.20 | 25 | 0/10 | n.s. |
|  | 5 | 2.92 | 32 | 0/9 | 0.05 |

The outstanding effect of Glomerellan against this type of tumour is shown by the 85% inhibition figure at 5 mg/g as compared with 32% inhibition by the commercial product Schizophyllan at the same does rate.

4. DBA/2-MC/SC-1 Fibrosarcoma

The tests reported at 3 above were repeated, the test period being 40 days. The results were as follows:

|  | Dose mg/kg | Average Tumour weight (g) | Inhibition % | Complete regression | Significance p < |
|---|---|---|---|---|---|
| Control |  | 4.1 | — | 0/11 | — |
| Glomerellan | 1 | 2.8 | 32 | 0/10 | n.s. |
|  | 5 | 0.7 | 83 | 6/10 | 0.0001 |
|  | 25 | 0.1 | 98 | 8/10 | 0.0001 |
| Schizophyllan | 5 | 1.5 | 63 | 1/10 | 0.0001 |

5. Noble-Nb-prostrate carcinoma

The effect of Glomerellan on synogeneic rat prostrate carcinoma was investigated by transplanting subcutaneously approximately one square millimeter sized tumour pieces into male noble rats. Treatment was started when the tumours had achieved a size of about 70 square millimeters. i.e. at day 17 after transplantation. Treatment lasted 4 weeks, the Schizophyllan and Glomerellan being injected interperitoneally in saline solution three times a week, the control animals being injected with the saline solution alone. In addition diethylstiboestrol, the oestrogenic hormone, injected subcutaneously, was incorporated into the test program. Results at day 45 are given below.

|  | Dose mg/kg | Average Tumour weight (g) | Inhibition % | Complete regression | Significance p < |
|---|---|---|---|---|---|
| Control | — | 8.0 | — | 0/7 | — |
| Diethyl-stilboestrol | 0.1 | 1.4 | 82 | 0/6 | 0.001 |
| Schizophyllan | 5.0 | 5.7 | 29 | 0/6 | n.s. |
| Schizophyllan + Diethyl stilboestrol | 5.0 0.1 | 0.4 | 95 | 0/6 | 0.0001 |
| Glomerellan | 5.0 | 4.2 | 48 | 0/6 | 0.05 |
| Glomerellan + Diethyl stilboestrol | 5.0 0.1 | 0.8 | 90 | 0/6 | 0.001 |

We claim:

1. A method of treating a tumour disease which comprises administering a therapeutically effective amount of the extracellular beta-glucan Glomerellan produced by Glomerella cingulata CMI CC 330957 or by mutants or variants thereof to immune-stimulate those in need thereof.

* * * * *